(12) United States Patent
Kuechler et al.

(10) Patent No.: US 9,278,897 B2
(45) Date of Patent: *Mar. 8, 2016

(54) PROCESS FOR PRODUCING PHENOL AND/OR CYCLOHEXANONE FROM CYCLOHEXYLBENZENE

(71) Applicant: ExxonMobil Chemical Patents Inc., Baytown, TX (US)

(72) Inventors: Keith H. Kuechler, Friendswood, TX (US); Jihad M. Dakka, Whitehouse Station, NJ (US); James R. Lattner, LaPorte, TX (US); Christopher L. Becker, Manhattan, KS (US); Edmund J. Mozeleski, Somerset, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/422,444

(22) PCT Filed: Sep. 12, 2013

(86) PCT No.: PCT/US2013/059496
§ 371 (c)(1),
(2) Date: Feb. 19, 2015

(87) PCT Pub. No.: WO2014/043371
PCT Pub. Date: Mar. 20, 2014

(65) Prior Publication Data
US 2015/0218075 A1    Aug. 6, 2015

Related U.S. Application Data

(60) Provisional application No. 61/734,213, filed on Dec. 6, 2012, provisional application No. 61/729,019, filed on Nov. 21, 2012, provisional application No. 61/701,997, filed on Sep. 17, 2012, provisional application No. 61/701,984, filed on Sep. 17, 2012.

(30) Foreign Application Priority Data

Feb. 13, 2013   (EP) .................................... 13155025

(51) Int. Cl.
| | | |
|---|---|---|
| C07C 45/53 | (2006.01) | |
| C07C 37/08 | (2006.01) | |
| C07C 2/66 | (2006.01) | |
| C07C 29/80 | (2006.01) | |
| C07C 1/24 | (2006.01) | |
| C07C 2/74 | (2006.01) | |
| C07C 5/03 | (2006.01) | |
| C07C 407/00 | (2006.01) | |
| C07C 29/60 | (2006.01) | |

(52) U.S. Cl.
CPC . *C07C 45/53* (2013.01); *C07C 1/24* (2013.01); *C07C 2/66* (2013.01); *C07C 2/74* (2013.01); *C07C 5/03* (2013.01); *C07C 29/60* (2013.01);

*C07C 29/80* (2013.01); *C07C 37/08* (2013.01); *C07C 407/00* (2013.01); *C07C 2101/14* (2013.01); *C07C 2529/70* (2013.01)

(58) Field of Classification Search
CPC ............ C07C 45/53; C07C 37/08; C07C 2/66
USPC .......................... 568/376, 798, 799; 585/467
See application file for complete search history.

(56) References Cited

U.S. PATENT DOCUMENTS

| | | | |
|---|---|---|---|
| 3,049,447 A | | 8/1962 | Knapp |
| 3,959,381 A | | 5/1976 | Arkell et al. |
| 4,147,726 A | | 4/1979 | Wu |
| 4,160,000 A | | 7/1979 | Hutto et al. |
| 4,358,618 A | | 11/1982 | Sifniades et al. |
| 4,439,409 A | * | 3/1984 | Puppe et al. .................. 423/706 |
| 4,954,325 A | * | 9/1990 | Rubin et al. .................. 423/706 |
| 5,250,277 A | * | 10/1993 | Kresge et al. .............. 423/329.1 |
| 6,037,513 A | | 3/2000 | Chang et al. |
| 6,720,462 B2 | | 4/2004 | Kuhnle et al. |
| 6,852,893 B2 | | 2/2005 | Kuhnle et al. |
| 2002/0169331 A1 | | 11/2002 | Miura et al. |
| 2011/0301387 A1 | | 12/2011 | Wang et al. |

FOREIGN PATENT DOCUMENTS

| | | |
|---|---|---|
| CN | 1962574 | 5/2007 |
| EP | 1074536 | 2/2001 |
| WO | WO2009/025939 | 2/2009 |
| WO | WO2009/058527 | 5/2009 |
| WO | WO2009/058531 | 5/2009 |
| WO | WO2009/128984 | 10/2009 |
| WO | WO2009/131769 | 10/2009 |
| WO | WO2010/098916 | 9/2010 |

(Continued)

*Primary Examiner* — Sikarl Witherspoon
(74) *Attorney, Agent, or Firm* — Siwen Chen; Stephen A. Baehl

(57) ABSTRACT

In a process for producing phenol and/or cyclohexanone, cyclohexylbenzene is contacted with an oxygen-containing gas to produce an oxidation effluent containing cyclohexylbenzene hydroperoxide. At least a portion of the cyclohexylbenzene hydroperoxide is then contacted with a cleavage catalyst to produce a cleavage effluent containing phenol and cyclohexanone and by-products including phenylcyclohexanol. The cleavage effluent or a neutralized product thereof also comprises at least one heteroatom-containing compound, which is separated from the cleavage effluent and/or the neutralized product thereof to leave a cleavage fraction lean in the heteroatom-containing compound and containing at least a portion of the phenylcyclohexanol. At least a portion of the phenylcyclohexanol is then contacted with a dehydration catalyst comprising a molecular sieve of the MCM-22 type to convert at least a portion of the phenylcyclohexanol to phenylcyclohexene.

22 Claims, 2 Drawing Sheets

(56) References Cited

FOREIGN PATENT DOCUMENTS

| WO | WO2012/036822 | 3/2012 |
| WO | WO2012/036826 | 3/2012 |
| WO | WO2012/036827 | 3/2012 |
| WO | WO2014/043188 | 3/2014 |
| WO | WO2014/043478 | 3/2014 |
| WO | WO2014/081597 | 5/2014 |
| WO | WO2014/088841 | 6/2014 |
| WO | WO2014/088842 | 6/2014 |

\* cited by examiner

PROCESS FOR PRODUCING PHENOL AND/OR CYCLOHEXANONE FROM CYCLOHEXYLBENZENE

PRIORITY CLAIM

This application is a National Stage Application of International Application No. PCT/US2013/059496, filed Sep. 12, 2013, which claims the benefit of U.S. Provisional Application Nos. 61/734,213 filed Dec. 6, 2012; 61/701,984, filed Sep. 17, 2012; 61/701,997, filed Sep. 17, 2012; 61/729,019, filed Nov. 21, 2012 and European Application No. 13155025.3, filed Feb. 13, 2013 the disclosures of which are fully incorporated herein by their reference.

FIELD

The present invention relates to a process for producing phenol and/or cyclohexanone.

BACKGROUND

Phenol and cyclohexanone are important materials in the chemical industry and are useful in, for example, the production of phenolic resins, bisphenol A, ε-caprolactam, adipic acid, plasticizers, and nylon polymers.

Currently, a common route for the production of phenol is the Hock process via cumene. This is a three-step process in which the first step involves alkylation of benzene with propylene in the presence of an acidic catalyst to produce cumene. The second step, is oxidation, preferably aerobic oxidation, of the cumene to the corresponding cumene hydroperoxide. The third step, is the cleavage of the cumene hydroperoxide in the presence of heterogeneous or homogenous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is via benzene hydroalkylation in which benzene is contacted with hydrogen in the presence of a catalyst such that a portion of the benzene is converted into cyclohexene which then reacts with the remaining benzene to produce the desired cyclohexylbenzene. One such method is disclosed in U.S. Pat. No. 6,037,513, in which the catalyst comprises a molecular sieve of the MCM-22 type and at least one hydrogenation metal selected from palladium, ruthenium, nickel, cobalt and mixtures thereof. This reference also discloses that the resultant cyclohexylbenzene can be oxidized to the corresponding hydroperoxide, which is then decomposed to the desired phenol and cyclohexanone co-products in roughly equimolar amounts.

Several technical challenges not seen in the cumene-based Hock process exist in producing phenol via cyclohexylbenzene. One such challenge is that non-negligible amounts of by-products, including phenylcyclohexanols, are generated during the oxidation and/or cleavage steps. To improve product yields, the phenylcyclohexanols is preferably dehydrated to phenylcyclohexene which can then be recycled to the oxidation step, either directly or, more desirably, after hydrogenation back to cyclohexylbenzene. However, the catalysts and conversion conditions suitable for effecting the dehydration reaction are also suitable for driving potential side reactions of phenylcyclohexene as well as any residual cyclohexylbenzene or desired product (cyclohexanone and phenol) that may be present in the dehydration feed. Thus, cyclohexanone can undergo aldol condensation to heavy products and phenol can be alkylated with phenylcyclohexene and cyclohexylbenzene. In addition, the phenylcyclohexene intermediate can undergo reactions such as dimerization, alkylation with residual cyclohexylbenzene, isomerization to other products, such as methylcyclopentylbenzene, and hydride transfer to biphenyl. Not only do these side reactions involve potential loss of valuable product, but they can also lead to deactivation of the dehydration catalyst.

SUMMARY

Investigation of this process has now shown that molecular sieves of the MCM-22 type are uniquely active and selective for the dehydration of the phenylcyclohexanols produced as by-products of the cleavage of cyclohexylbenzene hydroperoxide. However, the investigation has also shown that the cleavage effluent tends to include heteroatom-containing compounds (namely compounds containing atoms other than carbon, hydrogen, and oxygen), which can act as poisons to molecular sieve catalysts, such as MCM-22 and related materials. Sources of these heteroatom-containing compounds are believed to include nitrogen-containing compounds derived from the cyclic imides typically used to catalyze the cyclohexylbenzene oxidization reaction and sulfur-containing compounds derived from the sulfuric acid typically used to catalyze cleavage of the cyclohexylbenzene hydroperoxide. Other potential sources of heteroatom-containing compounds are acid-base complexation products generated on neutralization of the homogeneous acid catalysts typically used in the cleavage reaction.

The present invention seeks to provide a process for producing phenol and cyclohexanone which enables the selective catalytic dehydration of the phenylcyclohexanols by-product to phenylcyclohexene while minimizing catalyst poisoning by heteroatom-containing compounds.

Accordingly, in one aspect, the invention resides in a process for producing phenol and/or cyclohexanone, the process comprising:

(a) contacting cyclohexylbenzene with an oxygen-containing gas to produce an oxidation effluent containing cyclohexylbenzene hydroperoxide;

(b) contacting at least a portion of the oxidation effluent containing cyclohexylbenzene hydroperoxide with a cleavage catalyst to produce a cleavage effluent containing phenol, cyclohexanone, and by-products including phenylcyclohexanol;

(b1) optionally neutralizing the cleavage effluent to produce a neutralized product thereof;

wherein the cleavage effluent and/or the neutralized product thereof comprise at least one heteroatom-containing compound;

(c) separating at least a portion of the at least one heteroatom-containing compound from the cleavage effluent and/or the neutralized product thereof to produce a cleavage fraction containing at least a portion of the phenylcyclohexanol and at least 1.0% less of the at least one heteroatom-containing compound compared to before separating; and (d) contacting at least a portion of the cleavage fraction containing phenylcyclohexanol with a dehydration catalyst comprising a molecular sieve of the MCM-22 type to convert at least a portion of the phenylcyclohexanol to phenylcyclohexene.

In one embodiment, the contacting step (a) is conducted in the presence of an oxidation catalyst containing at least one heteroatom, such as nitrogen, and the cleavage effluent includes at least one heteroatom-containing compound derived from the oxidation catalyst. For example, the oxidation catalyst may comprise a cyclic imide.

In certain embodiments, the cleavage catalyst contains at least one heteroatom, such as sulfur, and the cleavage effluent includes at least one heteroatom-containing compound derived from the cleavage catalyst. For example, the cleavage catalyst may comprise sulfuric acid.

In certain embodiments, the cleavage effluent is contacted with a base to form the neutralized product containing an acid-base complexation compound containing at least one heteroatom. For example, the base may comprise at least one heteroatom, such as nitrogen.

DETAILED DESCRIPTION OF THE EMBODIMENTS

Figure 1:
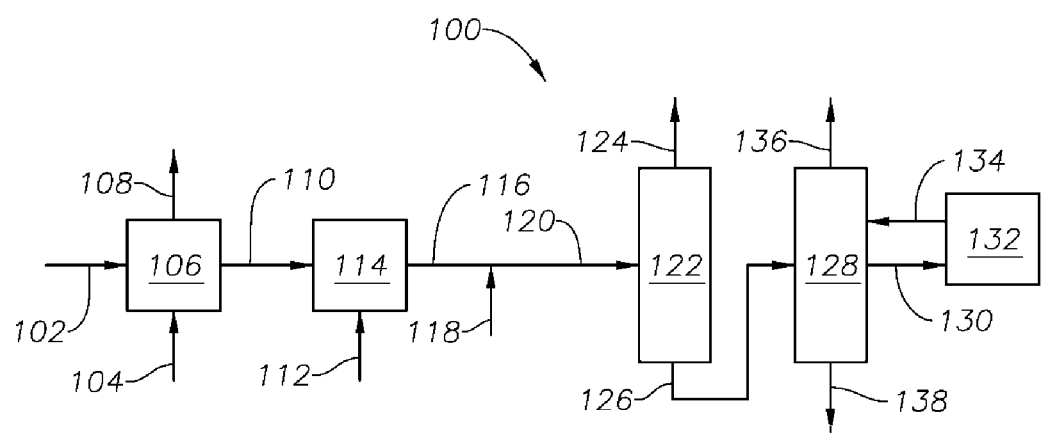
FIG. 1 is a flow diagram of a process for producing phenol and/or cyclohexanone according to a first embodiment of the present application.

In the present disclosure, a process may be described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two, or more hydrogenating metals are used, unless specified to the contrary or the context clearly indicates that only one hydrogenating metal is used.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzene, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

As used herein, the term "effluent" generally means the product of a given step or operation. Thus, the effluent can be a stream of material flowing from a vessel in a continuous process or the product from a batch or semi-batch process.

Described herein is a process for producing phenol and/or cyclohexanone from cyclohexylbenzene. In the process, the cyclohexylbenzene is initially oxidized to produce cyclohexylbenzene hydroperoxide, which is then contacted with a cleavage catalyst under conditions effective to produce a cleavage effluent containing the desired phenol and cyclohexanone. However, the oxidation step also produces by-products, including isomers of phenylcyclohexanol, which in the present process are catalytically dehydrated to phenylcyclohexene for recycle back to the oxidation step. In addition, it has now been found that one or more of the oxidation and cleavage steps tend to generate heteroatom-containing compounds (namely compounds containing atoms other than carbon, hydrogen, and oxygen), which can act as poisons to the dehydration catalyst. Similarly, where a homogeneous acid catalyst, such as sulfuric acid, is used to for the cleavage reaction, neutralization of the cleavage effluent can generate acid-base complexation products which also contain heteroatoms. In the present process, these heteroatom-containing compounds are at least partially removed from the cleavage effluent or its neutralized product so that the adverse affect of the heteroatoms on the dehydration catalyst is mitigated.

In one preferred embodiment, the present process forms part of an integrated process for producing phenol from benzene in which the benzene is initially alkylated or hydroalkylated to produce the cyclohexylbenzene feed to the present process. The ensuing description will therefore focus on this integrated process.

Production of Cyclohexylbenzene

The cyclohexylbenzene starting material for the present process can be produced by the alkylation of benzene with cyclohexene according to the following reaction:

The cyclohexene can be supplied to the reaction zone as a separate feed from the benzene, but normally is produced in situ by the selective hydrogenation of benzene in the presence of a bifunctional catalyst. In the case of cyclohexene being produced in situ, the overall a reaction is generally termed "hydroalkylation" and may be summarized as follows:

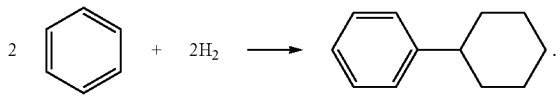 [SMILES: c1ccccc1 ; c1ccc(C2CCCCC2)cc1]

Any commercially available benzene feed can be used in the hydroalkylation step, but in one embodiment the benzene has a purity level of at least 99 wt %. Similarly, although the source of hydrogen is not critical, it is desirable that the hydrogen is at least 99 wt % pure.

In certain embodiments, the total feed to the hydroalkylation step contains less than 1000 ppm, such as less than 500 ppm, for example less than 100 ppm, water. In addition, the total feed may contain less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but the hydrogen supply is desirably arranged such that the molar ratio of hydrogen to benzene in the hydroalkylation feed is from about 0.15:1 to about 15:1, such as from about 0.4:1 to about 4:1, for example from about 0.4:1 to about 0.9:1.

In addition to the benzene and hydrogen, a diluent, which is substantially inert under hydroalkylation conditions, may be supplied to the hydroalkylation reaction. In certain embodiments, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, advantageously the diluent is added in an amount such that the weight ratio of the diluent to the aromatic compound is at least 1:100; for example at least 1:10, but no more than 10:1, for example no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating solid acid component. Advantageously, the alkylating solid acid component comprises a molecular sieve of the MCM-22 type. The term "MCM-22 type material" (or "material of the MCM-22 type" or "molecular sieve of the MCM-22 type"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth Edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 type generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof. Other molecular sieves, such as UZM-8 (described in U.S. Pat. No. 6,756,030), may be used alone or together with MCM-22 molecular sieves disclosed herein. Preferably, the molecular sieve is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. Desirably, the amount of hydrogenating metal present in the catalyst is from about 0.05 wt % to about 10 wt %, such as from about 0.1 wt % to about 5.0 wt %, of the catalyst. In one embodiment, where the MCM-22 type molecular sieve is an aluminosilicate, the amount of hydrogenating metal present is such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 type molecular sieve by, for example, impregnation or ion exchange. However, in certain embodiments, at least 50 wt %, for example at least 75 wt %, and desirably substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide, in certain embodiments by impregnation, before the metal-containing inorganic oxide is composited with the molecular sieve. In certain embodiments, the catalyst composite is produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 type molecular sieve catalyst is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene may be conducted in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking may also be effected in a reactor separate from the hydroalkylation reactor, such as a reactive distillation unit, at a temperature of about 150° C. to about 500° C. and a pressure of 15 psig to 500 psig (200 kPa to 3550 kPa gauge pressure) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia, and mixtures thereof. Desirably, the acid catalyst includes at least one aluminosilicate, aluminophosphate, or silicoaluminphosphate of the FAU, AEL, AFI, and MWW type. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is advantageously introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising of cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst desirably comprises (a) a support; (b) a hydrogenation-dehydrogenation component; and (c) an inorganic promoter. In certain embodiments, the support (a) is selected from the group consisting of silica, a silicate, an aluminosilicate, zirconia, carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Desirably, the hydrogenation-dehydrogenation component is present in an amount from about 0.1 wt % to about 10 wt % of the catalyst. A suitable inorganic promoter (c) comprises of at least one metal or compound thereof selected from Group 1 of the Periodic Table of Elements, such as a potassium compound. The promoter may be present in an amount from about 0.1 wt % to about 5.0 wt % of the catalyst. Suitable dehydrogenation conditions include a temperature of about 250° C. to about 500° C., a pressure of about atmospheric pressure to about 500 psig (100 kPa to 3550 kPa gauge pressure), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst is an acid catalyst in certain embodiments, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

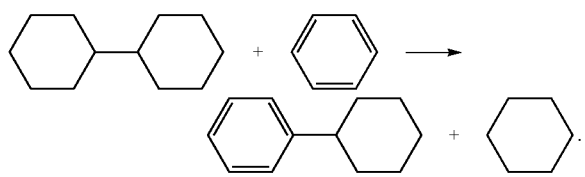

The catalytic treatment can be conducted on the direct product of the hydroalkylation reaction, or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation step can be conducted autogeneously, or more preferably, in the presence of a catalyst. Although any catalyst can be employed, a preferred oxidation catalyst includes an N-hydroxy substituted cyclic imide described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. In one embodiment, the catalyst is N-hydroxyphthalimide. Another suitable catalyst is N,N',N"-trihydroxyisocyanuric acid. Each of the above cyclic imide catalysts contain the heteroatom nitrogen.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5.0 wt %, of the cyclohexylbenzene.

Suitable conditions for the oxidation step include a temperature from about 70° C. to about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5.0 wt %, such as at least 10 wt %, for example at least 15 wt %, or at least 20 wt % cyclohexyl-1-phenyl-1-hydroperoxide based upon the total weight of the oxidation reaction effluent. Desirably, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

In addition to the desired cyclohexyl-1-phenyl-1-hydroperoxide (formula (F-I) below), the oxidation step tends to produce certain by-products which, if not removed and/or converted to useful materials would result in loss of valuable feed and/or could adversely influence downstream processes. Among these by-products are isomers of cyclohexyl-1-phenyl-1-hydroperoxide, including cyclohexyl-1-phenyl-2-hydroperoxide (formula (F-II) below), cyclohexyl-1-phenyl-3-hydroperoxide (formula (F-III) below), and cyclohexyl-1-phenyl-4-hydroperoxide (formula (F-IV) below). Other potential by-products are isomers of phenylcyclohexanol and phenylcyclohexanone, which may be generated in small amounts during the oxidation step but are mostly produced from the secondary isomers of cyclohexyl-1-phenyl-1-hydroperoxide during the subsequent cleavage step. Potential isomers of phenylcyclohexanol from either the oxidation or cleavage step include 1-phenyl-1-cyclohexanol (formula (F-V) below), 2-phenyl-1-cyclohexanol (formula (F-VI) below), 3-phenyl-1-cyclohexanol (formula (F-VII) below) and 4-phenyl-1-cyclohexanol (formula (F-VIII) below). As used herein, the generic term "phenylcyclohexanol" shall include at least one of these isomers and any mixture comprising two or more thereof at any proportion, unless specified or indicated otherwise. Potential isomers of phenylcyclohexanone from either the oxidation or cleavage step include 2-phenyl-1-cyclohexanone (formula (F-IX) below), 3-phenyl-1-cyclohexanone (formula (F-X) below) and 4-phenyl-1-cyclohexanone (formula (F-XI) below). As used herein, the generic term "phenylcyclohexanol," when used either in the singular or plural form, shall include all isomers thereof disclosed above and any mixtures comprising two or more of the isomers, unless specified or indicated to mean only one specific isomer. As used herein, the generic term "phenylcyclohexanone," when used either in the singular or plural form, shall include at least one of the isomers disclosed above and any mixtures comprising two or more thereof at any proportion, unless specified or otherwise indicated to mean only one specific isomer. As used herein, the term "2-phenyl isomers" include both 2-phenyl-1-cyclohexanol and 2-phenyl-1-cyclohexanone.

(F-I)
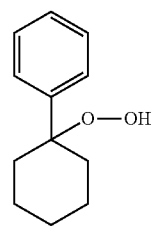

(F-II)
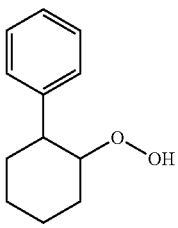

(F-III)
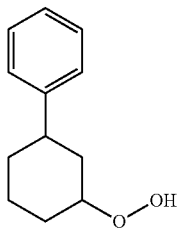

(F-IV)
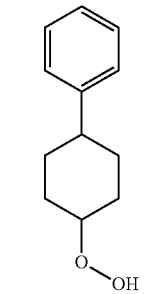

(F-V)
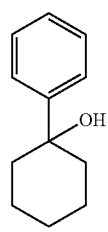

(F-VI)
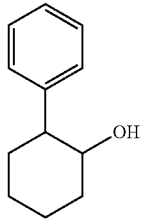

(F-VII)
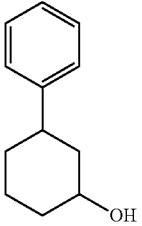

(F-VIII)
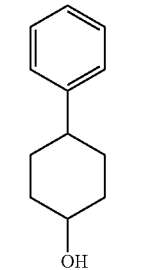

(F-IX)
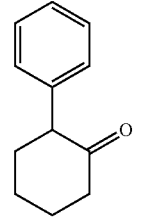

(F-X)
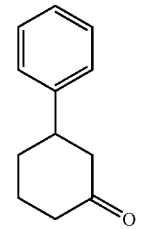

(F-XI)

In certain embodiments, the phenylcyclohexanols are present in the oxidation reaction effluent or in the cleavage effluent or a neutralized product thereof in an amount from 0.10 wt % to 10 wt % of the given effluent and the phenylcyclohexanones are present in an amount from 0.10 wt % to 5.0 wt % of the given effluent. In the present process, these by-products are removed and desirably converted to useful cyclohexylbenzene, which can then be recycled to the oxidation step. However, as explained below, removal and conversion of these by-products is desirably conducted after the cleavage step.

The oxidation reaction effluent will also contain some of the cyclic imide catalyst discussed above and, since the catalyst is expensive and can act as a poison to downstream HI reactions, it is desirable to remove and/or recover at least a portion of the catalyst from the oxidation reaction effluent for recycle back to the oxidation step. In one embodiment, removal of the cyclic imide comprises contacting the oxidation reaction effluent with an aqueous solution of a base, particularly a weak base having a pKb value greater than or equal to the pKa of the cyclic imide of the first catalyst, whereby the imide is extracted into the aqueous phase, leaving an organic phase which comprises the oxidized hydrocarbon product and a reduced level of cyclic imide. In another embodiment, treatment of the oxidation effluent to remove at least a portion of the cyclic imide comprises contacting the effluent with an effective solid sorbent, such as a metal oxide or a metal carbonate and/or hydrogen carbonate. However, irrespective of the method used to treat the oxidation reaction effluent, the feed to the cleavage reaction will generally contain up to 2500 ppm by weight, such as up to 1500 ppm by weight, of heteroatom-containing compounds from the cyclic imide catalyst.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

Prior to feeding to the cleavage step, the oxidation reaction effluent may be treated to increase the concentration of the cyclohexyl-1-phenyl-1-hydroperoxide. Suitable concentration steps include fractional distillation to remove at least a portion of the higher boiling cyclohexylbenzene and fractional crystallization to separate solid cyclohexyl-1-phenyl-1-hydroperoxide from the oxidation reaction effluent. In certain embodiments, the concentration step(s) are used to produce a cleavage feed containing greater than 40 wt % and no greater than 95 wt %, for example from 60 wt % to 85 wt %, of cyclohexyl-1-phenyl-1-hydroperoxide, and at least 5.0 wt % and less than 60 wt %, for example from 15 wt % to 40 wt %, of cyclohexylbenzene.

In the present process, the composition of cleavage feed is initially adjusted by mixing the cleavage feed with at least phenol, cyclohexanone, water, and sulfuric acid, to produce a cleavage reaction mixture containing from 15 wt % to 50 wt % phenol, from 15 wt % to 50 wt % cyclohexanone, from 1.0 wt % to 10 wt % cyclohexyl-1-phenyl-1-hydroperoxide, from 5.0 wt % to 60 wt % cyclohexylbenzene, from 0.10 wt % to 4.0 wt % water, and from 10 wppm to 1000 wppm sulfuric acid. In one embodiment, the cleavage reaction mixture contains from 25 wt % to 45 wt % phenol, from 25 wt % to 45 wt % cyclohexanone, from 1.0 wt % to 6 wt % cyclohexyl-1-phenyl-1-hydroperoxide, from 15 wt % to 40 wt % cyclohexylbenzene, from 0.5 wt % to 3.0 wt % water, and from 20 wppm and to 500 wppm sulfuric acid. In another embodiment, the cleavage reaction mixture contains from 30 wt % to 40 wt % phenol, from 30 wt % to 40 wt % cyclohexanone, from 1.0 wt % to 5.0 wt % cyclohexyl-1-phenyl-1-hydroperoxide, from 15 wt % to 40 wt % cyclohexylbenzene, from 0.5 wt % to 2.0 wt % water, and from 40 wppm and to 200 wppm sulfuric acid. In yet another embodiment, the cleavage reaction mixture contains at least 1.0 wt % more phenol than the wt % of cyclohexanone, for example so that the weight ratio of phenol to cyclohexanone in the cleavage reaction mixture is in excess of 1:1, desirably from 1.05:1 to 10:1.

Adjustment of the composition of the cleavage feed may be achieved by mixing the cleavage feed with a recycle stream comprising a portion of the cleavage effluent since the latter contains phenol, cyclohexanone, cyclohexyl-1-phenyl-1-hydroperoxide, cyclohexylbenzene, water, and sulfuric acid. In some embodiments, mixing with the cleavage recycle stream may be sufficient to achieve the desired reaction mixture composition. Where necessary, however, the desired water content in the cleavage reaction mixture can be obtained by one or more of adding water to the cleavage feed, mixing the cleavage feed with the cleavage recycle stream and with water, adding water to the cleavage recycle stream, and adding water to the cleavage effluent. Similarly, the desired sulfuric acid content in the cleavage reaction mixture can be obtained by one or more of adding sulfuric acid to the cleavage feed, mixing the cleavage feed with the cleavage recycle stream and with sulfuric acid, adding sulfuric acid to the cleavage recycle stream, and adding sulfuric acid to the cleavage effluent. In addition, the desired phenol content in the cleavage reaction mixture can be obtained by one or more of adding phenol to the cleavage feed, mixing the cleavage feed with the cleavage recycle stream and with phenol, adding phenol to the cleavage recycle stream, and adding phenol to the cleavage effluent.

The cleavage reaction is conducted under conditions including a temperature from 30° C. and to 70° C., such as from 40° C. to 60° C. and a pressure of at least 1 atmosphere, such as from 100 KPaa to 2000 kPaa). The cleavage conditions are desirably selected so that the cleavage reaction mixture is completely or predominantly in the liquid phase during the cleavage reaction and so that the reaction occurs at a cyclohexyl-1-phenyl-1-hydroperoxide (CHBHP) first order rate constant from 0.1 $min^{-1}$ to 20 $min^{-1}$. Alternatively, the CHBHP first order rate constant may be from 0.5 $min^{-1}$ to 15 $min^{-1}$, or from 1 $min^{-1}$ to 12 $min^{-1}$ In one embodiment, the cleavage reaction is conducted for a time sufficient to convert at least 50%, desirably at least 75%, of the cyclohexyl-1-phenyl-1-hydroperoxide in the cleavage reaction mixture and produce a cleavage effluent containing phenol and cyclohexanone.

Desirably, the acid catalyst used in the cleavage reaction is at least partially soluble in the cleavage effluent, is stable at a temperature of at least 185° C. and has a lower volatility (higher normal boiling point) than cyclohexylbenzene. Desirably, the acid catalyst is also at least partially soluble in the cleavage reaction product. Suitable homogeneous acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In other embodiments, a heterogeneous acid catalyst is employed for the cleavage reaction, such as molecular sieve, and in particular a molecular sieve having a pore size in excess of 6.1 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. In one embodiment, the polar solvent is phenol and/or cyclohexanone recycled from the cleavage product after cooling. Advantageously, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction, but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range.

In various embodiments, the cleavage reactor is operable to transport a portion of the contents through a cooling device and return the cooled portion to the cleavage reactor, thereby managing the exothermicity of the cleavage reaction. In one embodiment, cooling coils operating within the cleavage reactor(s) remove any heat generated. Alternatively, the reactor may be operated adiabatically. In another embodiment, the cleavage effluent taken from the cleavage reactor is cooled and at least a portion of the cooled cleavage effluent is divided into a cooled cleavage recycle to be mixed with the cleavage feed.

The major products of the cleavage reaction are phenol and cyclohexanone, which are present in substantially equimolar amounts and, by virtue of the present process, are obtained in high yield. As discussed above, typical primary by-products of the cleavage of cyclohexyl-1-phenyl-1-hydroperoxide include the β-scission products such as hexanophenone and 6-hydroxylhexanophenone (6-HHP). Examples of secondary by-products include those derived from cyclohexanone, such as 2-(1-cyclohexenyl)cyclohexanone, 2-(cyclohexylidene) cyclohexanone (cyclohexanone aldol condensation products), 2-hydroxycyclohexanone, and cyclohexenone (cyclohexanone oxidation products). In the present process the formation of these by-products is reduced so that, for example, the amount of 6-hydroxylhexanophenone (6-HHP) in the cleavage effluent may be no greater than 5.0 wt %, or no greater than 2.0 wt %.

On leaving the cleavage reactor, the cleavage effluent may be cooled and thereafter separated into a product stream, from which the phenol and cyclohexanone products can be recovered, and a cleavage recycle stream, which can be mixed with the cleavage feed. Separation of the cleavage recycle stream can be effected without prior modification of the composition of cleavage effluent so that the recycle stream is composed of an aliquot of the cleavage effluent. In one embodiment, the cleavage recycle has substantially the same composition as the cleavage effluent, say within 2.0 wt % or even within 1.0 wt % of any given species content in the cleavage effluent, for example, as may be indirectly affected by reactions occurring on the cleavage recycle in conveyance to the mixing with the cleavage feed. Thus, the cleavage feed may further be mixed with cyclohexylbenzene, in addition to at least phenol, cyclohexanone, water and sulfuric acid, for example, as may all be present in the portion of the cleavage effluent allocated as cleavage recycle.

Alternatively, the cleavage effluent or a portion thereof can be treated, for example, by fractionation, to separate the by-products and/or other components of the cleavage effluent. These components may include phenol, cyclohexanone, and water, which may be used to provide at least some of the phenol, cyclohexanone, or water for mixing with the cleavage feed to attain the desired cleavage reaction mixture composition.

In addition to the products and by-products described above, the cleavage effluent contains certain heteroatom-containing compounds, such as N-containing compounds derived from the oxidation catalyst. In some embodiments, the effluent from cleavage reaction also contains residual sulfuric acid cleavage catalyst. In this case, the residual sulfuric acid in the cleavage reaction effluent is initially neutralized by treating the cleavage effluent with one or more basic compounds. Suitable basic compounds include amines or diamines, for example 2-methylpentane-1,5 diamine, and neutralization of the cleavage effluent produces acid-base complexation compounds containing at least one heteroatom, such as nitrogen and/or sulfur.

Treatment of the Cleavage Reaction Effluent

In the present process, at least a portion of the phenylcyclohexanol present in the cleavage effluent is dehydrated over a catalyst comprising a molecular sieve of the MCM-22 type to produce phenylcyclohexene for direct or indirect recycle to oxidation step. However, since the heteroatom-containing compounds present in the cleavage effluent can act as poisons to molecular sieve catalysts, such as MCM-22, the cleavage effluent or the neutralized product thereof is initially subjected to one or more separation steps to remove at least a portion of the heteroatom-containing compounds. Because of the very low volatility of the heteroatom-containing compounds relative to the phenol, cyclohexanone, phenylcyclohexanol, and cyclohexylbenzene present in the cleavage effluent, the separation can readily be effected by effluent by distillation, even a single stage vapor-liquid flash operation. Thus, in the course of a single stage flash or multi-stage distillation operation, feeding liquid cleavage effluent containing phenylcyclohexanol, almost no heteroatom-containing compound will be in the vapor phase across a very wide range of conditions, in particular, at the same conditions wherein large amounts of phenol, cyclohexanone, phenylcyclohexanol and cyclohexylbenzene will be in the vapor phase. The vapor phase fraction can then be sent to dehydration, normally after condensation back to the liquid phase.

A desirable form of separation is the use of fractional distillation, wherein the cleavage effluent is fed to a distillation column. A vapor stream may be taken anywhere in the column, conveniently below the feed tray where the concentration of phenylcyclohexanol relative to cyclohexylbenzene is relatively high compared to the feed. A liquid stream may be taken at any point above the feed tray, such material having undergone at least one vapor-liquid flash at the feed tray itself. In one embodiment, it will be taken at least two trays above the feed tray, to reduce the amount of heteroatom-containing compounds that may be present due to liquid entrainment in the vapor moving from a given tray to the tray above, but no more than about 6 trays above the feed tray, again, to maintain a relatively high concentration of phenylcyclohexanol in the fraction to be sent to dehydration.

A convenient form of fractional distillation is a dividing wall column. Dividing wall columns are known in the art, e.g., as described in 0. Yildirim, et al., "Dividing Wall Columns in Chemical Process Industry: A Review on Current Activities", Separation and Purification Technology Vol. 80, (2011) pp. 403-417, the entire contents of which are incorporated herein by reference. In a dividing wall column, one side of the column where the feed (cleavage product or neutralized cleavage product or stream derived therefrom containing phenycyclohexanol and heteroatom-containing compounds) is introduced is called the feed side. The other side of the column is the anti-feed side. In the anti-feed side, all of the material presented is derived from the vapor phase of the trays of the feed side, and hence there will be little or no heteroatom-containing compounds present in the anti-feed side. A liquid may be withdrawn from the anti-feed side of the dividing wall distillation column and provided to dehydration. By this method, a heteroatom-lean cleavage effluent or complexation product-lean cleavage effluent may conveniently be formed with advantageous composition, rich in phenylcyclohexanol and lean in cyclohexylbenzene to provide to dehydration.

The entire cleavage effluent may be fed to the separation step for removing the heteroatom-containing compounds, but in a more desirable embodiment the phenol and cyclohexanone are initially removed from the cleavage effluent, for example in a separate distillation column.

In one embodiment, the separation step(s) reduce the concentration of the heteroatom-containing compounds in the heteroatom-lean cleavage fraction to no greater than 1000 wppm, 100 wppm, or 10 wppm, or 1 wppm, or have no detectable heteroatom content.

Dehydration of the phenylcyclohexanols to phenylcyclohexene is effected over a solid acid catalyst comprising a molecular sieve of the MCM-22 type. In one embodiment, the molecular sieve of the MCM-22 type is MCM-49 or MCM-56. The catalyst may also contain an inorganic oxide binder, such as silica, alumina or silica/alumina. The dehydration reaction is advantageously conducted at a temperature of 25° C. to 200° C., such as 80° C. to 150° C., a pressure of 15 kPa to 500 kPa and a weight hourly space velocity of 0.1 $hr^{-1}$ to 50 $hr^{-1}$. The products of the dehydration reaction include 2-phenyl-1-cyclohexene (formula (F-XII) below), 3-phenyl-1-cyclohexene (formula (F-XIII) below) and 4-phenyl-1-cyclohexene (formula (F-XIV) below). As used herein, the generic term "phenylcyclohexene," when used either in singular or plural form, includes all the isomers disclosed above and any mixtures of two or more thereof, unless specified or otherwise indicated to mean only one specific isomer.

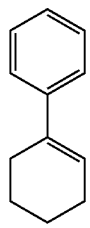

(F-XII)

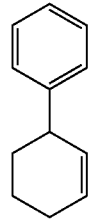

(F-XIII)

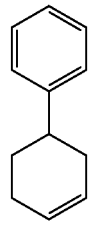

(F-XIV)

The phenylcyclohexene-containing product of the dehydration reaction may be recycled directly to the oxidation reaction, although levels of phenylcyclohexene above 1000 ppm by weight may be detrimental to the generation of the free radicals involved in the oxidation process. In other embodiments, therefore, the dehydration product is hydrogenated to convert the phenylcyclohexene to cyclohexylbenzene before the product is recycled to oxidation. In one embodiment, the hydrogenation is effected by contacting the phenylcyclohexene-containing product with hydrogen in a hydrogenation reaction zone, which is advantageously operated at a temperature of 80° C. to 150° C., such as 80° C. to 120° C., and a hydrogen partial pressure of 15 kPa to 1000 kPa, such as 15 kPa to 300 kPa. The hydrogenation is desirably conducted in the presence of a catalyst comprising at least one metal selected from Groups 6 to 12 of the Periodic Table of Elements, preferably palladium, on an inorganic support, such as silica.

The dehydration and hydrogenation reactions can be conducted sequentially in separate reactors or in stacked beds in the same reactor.

In some embodiments, it may be desirable to take a vapor or liquid side draw from either the distillation column used to remove the amine salts or from the distillation column used to separate the phenylcyclohexanol and/or phenylcyclohexanone by-products and employ this side draw as a feed to the dehydration/hydrogenation reactor. This would also allow integration of the distillation columns with the dehydration/hydrogenation reactor such that the effluent from the reactor could be fed back into the distillation column(s) to remove impurities produced in the dehydration/hydrogenation reaction.

The invention will now be more particularly described with reference to the accompanying drawings.

FIG. 1 is a flow diagram of a process 100 for producing phenol and/or cyclohexanone according to a first embodiment of the present application, in which a feedstock comprising cyclohexylbenzene is provided by line 102 to an oxidation reactor 106. A stream comprising oxygen, conveniently air, is also provided to the oxidation reactor 106 by way of line 104. Conditions within oxidation reactor 106 are such that cyclohexylbenzene in the feedstock is oxidized to form cyclohexylbenzene hydroperoxide. In one embodiment, an oxidation catalyst, such as the heteroatom containing-compound N-hydroxyphthalimide (NHPI), is also introduced to oxidation reactor 106, by means not shown in FIG. 1, to facilitate the oxidation reaction.

As the oxidation reaction continues, oxygen is depleted and an oxygen depleted stream in line 108 is removed from oxidation reactor 106. When the oxidation reaction is conducted at or near atmospheric pressure, the oxygen depleted stream in line 108 may also contain lower volatility by-products of the oxidation reaction, such as water, along with minor amounts of cyclohexylbenzene. In an operation not shown in FIG. 1, the oxygen depleted stream in line 108 may be further processed to recover the cyclohexylbenzene, remove water, and otherwise make the cyclohexylbenzene suitable for recycle to the oxidation reactor 106, and make other streams suitable for other uses or disposal.

An oxidation reaction product including cyclohexylbenzene hydroperoxide, desirably rich in cyclohexyl-1-phenyl-1-hydroperoxide but potentially including other hydroperoxides and dihydroperoxides, and in one embodiment comprising phenylcyclohexanols, is withdrawn from oxidation reactor 106 by way of line 110. In an embodiment where NHPI is introduced to the oxidation reactor 106, the oxidation reaction product may also contain NHPI.

The oxidation reaction product in line 110 is fed to a cleavage reactor 114, which also receives a homogeneous acid catalyst by way of line 112. In the embodiment shown, the acid catalyst in line 112 is sulfuric acid or a mixture of sulfuric acid and water, i.e., a catalyst containing the heteroatom sulfur. Conditions in cleavage reactor 114 are such that a cleavage reaction takes place, causing the cyclohexyl-1-phenyl-1-hydroperoxide to decompose to products including phenol and cyclohexanone, and in one embodiment also producing phenylcyclohexanols, e.g., from the decomposition of hydroperoxides other than cyclohexyl-1-phenyl-1-hydroperoxide. A cleavage effluent including phenol, cyclohexanone, and phenylcyclohexanols is withdrawn from cleavage reactor 114 by way of 116. In one embodiment, the cleavage effluent includes some of the heteroatom-containing acid cleavage catalyst, the heteroatom-containing oxidation catalyst, or both.

The cleavage effluent in line 116 is mixed with a heteroatom base, such as a relatively high molecular weight amine, for example, 2-methylpentane-1,5-diamine, in line 118 to complex with and neutralize the sulfuric acid in the cleavage effluent in line 116, creating a neutralized cleavage effluent in line 120. The neutralized cleavage effluent in line 120 thus now comprises phenol, cyclohexanone, phenylcyclohexanols, NHPI and an acid-base complexation product that is an amine-sulfuric acid salt(s). Conveniently, the salt is completely soluble in the balance of the neutralized cleavage effluent materials contained in the remaining elements of the method of the present invention, and further has a relatively low volatility compared to cyclohexylbenzene.

The neutralized cleavage effluent in line 120 is directed to a separation device, for example, a first fractionation column 122, which is operated to separate a first overhead product from the neutralized cleavage effluent. The first overhead product is removed from the fractionation column 122 in line 124 and in one embodiment is rich in phenol, cyclohexanone and components of a lower volatility than phenol, and includes a low amount, for example, no greater than 5.0 wt %, or no greater than 2.0 wt %, or no greater than 0.1 wt %, of cyclohexylbenzene. The first overhead product is fed by line 124 to a product treatment section (not shown) where the phenol and cyclohexanone are recovered and purified.

First fractionation column 122 is further operated to produce from the neutralized cleavage effluent a first bottoms product that is removed from the column 122 in line 126. In one embodiment, the first bottoms product in line 126 is rich in cyclohexylbenzene, phenylcyclohexanols, and components of lower volatility that cyclohexanols, and includes a low amount of light components, such as pentanal, hexanal, methylcyclopentanone, cyclohexanone, and phenol. For example, the first bottoms product may comprise no greater than 1.0 wt %, or no greater than 0.1 wt %, or even no greater than 100 wppm of water, pentanal, hexanal, methylcyclopentanone, cyclohexanone, and phenol combined. The first bottoms product also contains heteratom compounds derived from one or more of the oxidation catalyst, the cleavage catalyst and the acid-base complexation product resulting from neutralization of the cleavage catalyst.

The first bottoms product in line 126 is provided to a further separation device, for example, a second fractionation column 128, which is operated to separate a second overhead product from the first bottoms product. The second overhead product is removed from the fractionation column 128 in line 136 and in one embodiment is rich in cyclohexylbenzene and phenylcyclohexene, and has a low concentration, e.g., no greater than 1000 wppm, of oxygenated hydrocarbons, such as 1-phenylhexan-1-one. The second overhead product in line 136 is recycled to the oxidation reactor 106, optionally after first passing it through a hydrogenation unit to convert phenylcyclohexene to cyclohexylbenzene.

Further, the second fractionation column 128 is operated to produce a second bottoms stream that is removed from second fractionation column 128 in line 138. In one embodiment, the second bottoms stream in line 138 is rich in heavy oxygenated compounds, e.g., 1-phenylhexan-1-one, phenylcyclohexanones, phenylcyclohexanols, and 6-hydroxyhexaphenone, and contains a low amount, for example, no greater than 5.0 wt %, or no greater than 2.0 wt %, or no greater than 0.1 wt %, of cyclohexylbenzene and phenylcyclohexene, cyclohexylbenzene, and phenylcyclohexene combined. The second bottoms stream in line 138 further includes the vast majority of the heteroatom-containing compounds that are present in the first bottoms product in line 126, for example, at least 99 wt %, or at least 99.9 wt %, or 100 wt %, relative to the total amount of heteroatom-containing compounds in the first bottoms product in line 126. The second bottoms stream will generally be purged from the process, and potentially used as a combustion fuel.

A liquid sidestream is withdrawn via line 130 from a tray of the second fractionation column 128 at least one tray above the feed tray of second fractionation column 128. The liquid sidestream in line 130 contains cyclohexylbenzene, phenylcyclohexene and phenylcyclohexanols, and may further contain some heavy oxygenated compounds. Having been withdrawn the specified location, the liquid sidestream in line 130 is derived from a vapor flash of the neutralized cleavage effluent in line 120, and will have a very low concentration of heteroatom-containing compounds, for example, less than 10 wppm or even having no detectable amount of heteroatom-containing compounds relative to the total weight of material in line 130.

The liquid sidestream in line 130, containing phenylcyclohexanols, is provided to a dehydration reactor 132, where it is contacted with a dehydration catalyst comprising MCM-56 under conditions effective to convert at least a portion of the phenylcyclohexanol to phenylcyclohexene, and create a dehydration effluent. The dehydration effluent exits the dehydration reactor 132 in line 134 and is returned as a second feed to second fractionation column 128, conveniently to a tray above that from which the liquid sidestream is withdrawn. By virtue of the relative volatilities of phenylcyclohexene and phenylcyclohexanol, and with proper selection of the second feed location and operation of second fractionation column 128, this allows the phenylcyclohexene in the dehydration effluent to readily exit the column 128 in the overhead line 136, avoiding re-contacting with the dehydration catalyst, while allowing unconverted phenylcyclohexanol to proceed down the column for withdrawal with the liquid sidestream in line 130.

Along with phenylcyclohexene, water may also enter second fractionation column 128 with the dehydration effluent in line 134, as a co-product of the dehydration of penylcyclohexanols in dehydration reactor 132. Second fractionation column 128 may be fitted with means (not shown), to properly manage the production of water, e.g. a water boot in a condenser drum on the overhead product circuit with a separate line for withdrawal. Additionally, rather than an overhead product, the cyclohexylbenzene and phenylcyclohexene product in line 136 may be taken from second fractionation column 128 as a further liquid sidestream at a point near the top of the column, to provide that product with a reduced content of water for subsequent processing and eventual recycle to oxidation reactor 106.

Figure 2:
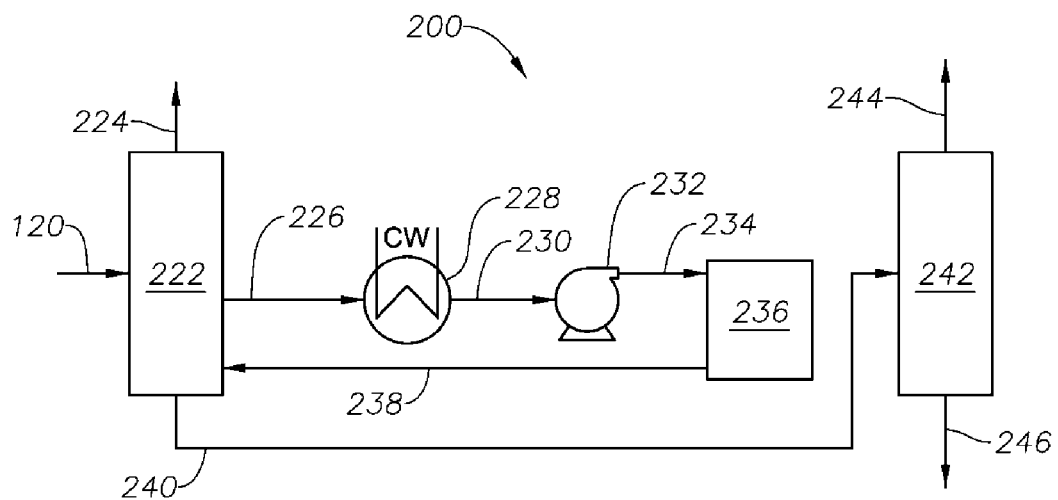
FIG. 2 is a flow diagram of a portion of a process for producing phenol and/or cyclohexanone according to a second embodiment of the present application.

Referring now to FIG. 2, the process of the second embodiment 200 employs the same oxidation, cleavage and cleavage neutralization steps as the process shown in FIG. 1 to produce a neutralized cleavage effluent which is fed by line 120 to a separation device, for example, first fractionation column 222. First fractionation column 222 is operated to separate the neutralized cleavage effluent into a first overhead product that is removed in line 224 and a first bottoms product that is removed in line 240. The first overhead product in line 224 is rich in phenol, cyclohexanone and components of a lower volatility than phenol, and includes a low amount, for example, no greater than 5.0 wt %, or no greater than 2.0 wt %, or no greater than 0.1 wt %, of cyclohexylbenzene. The first overhead product is fed by line 224 to a product treatment section (not shown) where the phenol and cyclohexanone are recovered and purified.

The first bottoms product in line 240 is rich in cyclohexylbenzene, phenylcyclohexenes and components of lower volatility than phenylcyclohexenes, and includes a low amount of light components, for example, water, pentanal, hexanal, methylcyclopentanone, cyclohexanone, and phenol, comprising no greater than 1.0 wt %, or no greater than 0.1 wt %, or even no greater than 100 wppm of water, pentanal, hexanal, methylcyclopentanone, cyclohexanone, and phenol combined. The first bottoms product also contains heteroatom compounds derived from one or more of the oxidation catalyst, the cleavage catalyst and the acid-base complexation product resulting from neutralization of the cleavage catalyst.

First fractionation column 222 is also operated to withdraw a heteroatom lean cleavage effluent in line 226 as a vapor sidestream from a tray below the feed tray into which the neutralized cleavage effluent in line 120 of FIG. 2 is provided. Conveniently, the vapor sidestream in line 226 is rich in cyclohexylbenzene, phenylcyclohexanols, and components of lower volatility than phenylcyclohexanols, and includes a low amount of light components, for example, water, pentanal, hexanal, methylcyclopentanone, cyclohexanone, and phenol, comprising no greater than 1.0 wt %, or no greater than 0.1 wt %, or even no greater than 100 wppm of water, pentanal, hexanal, methylcyclopentanone, cyclohexanone, and phenol combined. The heteroatom lean cleavage effluent in line 226 is derived from a vapor flash of the neutralized cleavage effluent in line 120, and will have a very low concentration, for example, less than 10 wppm or even having no detectable amount, of heteroatom-containing compounds, relative to the total weight of material in the heteroatom lean cleavage effluent in line 226.

The heteroatom lean cleavage effluent in line 226 is provided to a cooler 228, e.g., a cooling water indirect heat exchanger, to convert the vapor to a liquid heteroatom lean cleavage effluent in line 230 at a desired temperature. The liquid heteroatom lean cleavage effluent in line 226 is provided to pump 232 to increase the pressure of the liquid to a desired value, resulting in a pressurized liquid heteroatom lean cleavage effluent in line 234. The resultant pressurized liquid heteroatom lean cleavage effluent is provided to a dehydration reactor 236, where it is contacted with a dehydration catalyst comprising MCM-56 under conditions effective to convert at least a portion of the phenylcyclohexanol to phenylcyclohexene, and create a dehydration effluent in line 238. The dehydration effluent in line 238 is returned as a second feed to the first fractionation column 222, conveniently to a tray below that from which the heteroatom lean cleavage effluent in line 226 is withdrawn. By virtue of the relative volatilities of phenylcyclohexene and phenylcyclohexanol, and with proper selection of the second feed location to and operations of second fractionation column 128, this allows the phenylcyclohexene to exit the column bottoms and avoid re-contact with the dehydration catalyst.

Along with phenylcyclohexene, water may also enter first fractionation column 222 with the dehydration effluent in line 238, as a coproduct of the dehydration of phenylcyclohexanols in dehydration reactor 236. First fractionation column 222 may be fitted with means (not shown), to properly manage the production of water, e.g., a water boot in a condenser drum on the overhead product circuit with a separate line for withdrawal.

The first bottoms product in line 240 is provided to a further separation device, for example, second fractionation column 242, which is operated to separate the first bottoms product into a second overhead product that is removed from the column 242 in line 244 and a second bottoms stream which is removed in line 246. In one embodiment, the second fractionation column 242 is operated so that the second overhead product in line 244 is rich in cyclohexylbenzene and phenylcyclohexene, and has a low concentration, e.g., no greater than 1000 wppm of oxygenated hydrocarbons and, in particular, no greater than 1000 wppm of 1-phenylhexan-1-one. The second overhead product in line 244 is recycled to the oxidation reactor (not shown), optionally after first passing it through a hydrogenation unit to convert phenylcyclohexene to cyclohexylbenzene.

Further, the second fractionation column 242 is operated so that the second bottoms stream which is removed in line 246 is rich in heavy oxygenated compounds, e.g., 1-phenylhexan-1-one, phenylcyclohexanones, phenylcyclohexanols and 6-hydroxyhexaphenone, and contains a low amount, for example, no greater than 5.0 wt %, or no greater than 2.0 wt %, or no greater than 0.1 wt %, of cyclohexylbenzene and phenylcyclohexene combined. The second bottoms stream further includes the vast majority of the heteroatom-containing compounds that were present in the first bottoms product in line 240, for example, at least 99 wt %, or at least 99.9 wt %, or 100 wt %, relative to the total amount of the heteroatom-containing compounds in the first bottoms product in line 240. The second bottoms stream will generally be purged from the process.

Figure 3:
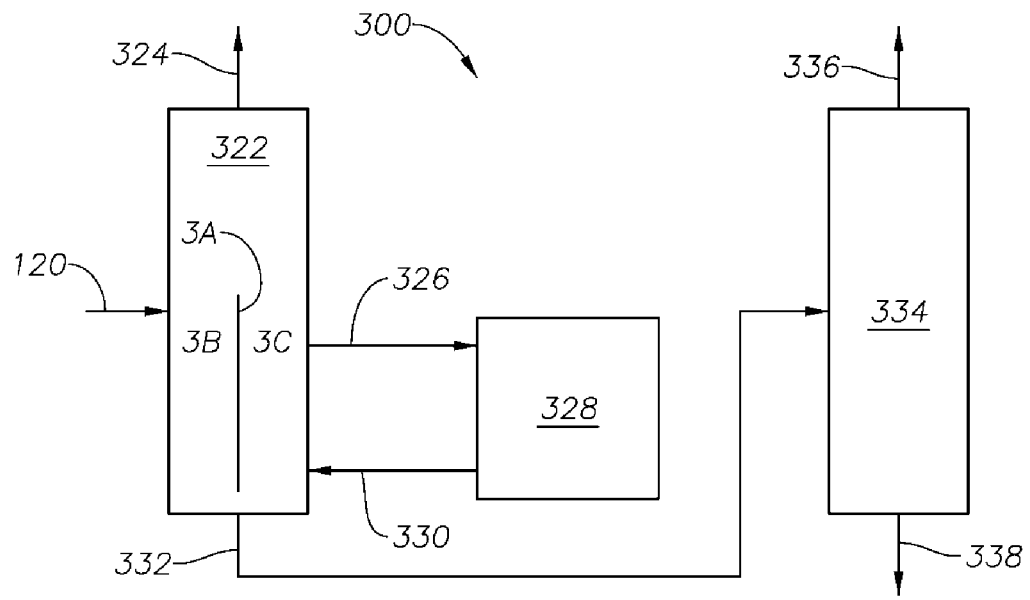
FIG. 3 is a flow diagram of a portion of a process for producing phenol and/or cyclohexanone according to a third embodiment of the present application.

Referring now to FIG. 3, the process of the third embodiment 300 also employs the same oxidation, cleavage and cleavage neutralization steps as the process shown in FIG. 1 to produce a neutralized cleavage effluent which is fed by line 120 to a separation device, for example, first fractionation column 322. First fractionation column 322 comprises a dividing wall 3A which extends across the entire diameter or fully across a suitable chord of first fractionation column 322 to form two discrete sections 3B and 3C without vapor or liquid communication therebetween. Further, dividing wall 3A runs axially in first fractionation column 322 from a point above at least the liquid level of the feed tray to which the neutralized cleavage effluent in line 120 is directed to a point above the reboiler sump liquid level near the bottom of the column 322. Dividing wall 3A ensures that section 3C is not be exposed to the liquid material, and hence the heteroatoms, present in the neutralized cleavage effluent in line 120, but rather all the liquid in section 3C comes from the reflux generated in the overhead circuit (not shown in FIG. 3) of first fractionation column 322. This reflux and hence the liquid in section 3C is derived from a vapor flash of the neutralized cleavage effluent within first fractionation column 322, i.e., the reboiler vapors from of bottoms circuit (not shown in FIG. 3) flowing up through both sections 3B and 3C. Section 3B is the feed side, while section 3C is the anti-feed side of dividing wall first fractionation column 322.

First fractionation column 322 is operated to divide the neutralized cleavage effluent into a first overhead product that is removed from fractionation column 322 in line 324 and a first bottoms product that is removed in line 332. In one embodiment, the first overhead product in line 324 is rich in phenol, cyclohexanone and components of a lower volatility than phenol, and includes a low amount, for example, no greater than 5.0 wt %, or no greater than 2.0 wt %, or no greater than 0.1 wt %, of cyclohexylbenzene. The first overhead product is fed by line 324 to a product treatment section (not shown) where the phenol and cyclohexanone are recovered and purified.

The first bottoms product in line 332 is rich in cyclohexylbenzene, phenylcyclohexenes and components of lower volatility than phenylcyclohexenes, such as any heteroatom-containing compounds, and includes a low amount of light components, for example, water, pentanal, hexanal, methylcyclopentanone, cyclohexanone, and phenol, comprising no greater than 1.0 wt %, or no greater than 0.1 wt %, or even no greater than 100 wppm of water, pentanal, hexanal, methylcyclopentanone, cyclohexanone, and phenol combined. The first bottoms product also contains heteratom compounds derived from one or more of the oxidation catalyst, the cleavage catalyst and the acid-base complexation product resulting from neutralization of the cleavage catalyst.

First fractionation column 322 is also operated to withdraw a heteroatom lean cleavage effluent in line 326 as a liquid sidestream from anti-feed side section 3C, conveniently from a tray below the feed tray into which the neutralized cleavage effluent is provided. Conveniently, heteroatom lean cleavage effluent in line 326 is rich in cyclohexylbenzene, phenylcyclohexanols and components of lower volatility than phenylcyclohexanols, and includes a low amount of light components, for example, water, pentanal, hexanal, methylcyclopentanone, cyclohexanone, and phenol, comprising no greater than 1.0 wt %, or no greater than 0.1 wt %, or even no greater than 100 wppm of water, pentanal, hexanal, methylcyclopentanone, cyclohexanone and phenol combined. As discussed earlier, the heteroatom lean cleavage effluent in line 326 taken from anti-feed section 3C is derived from a vapor flash of the neutralized cleavage effluent in line 120 and will have a very low concentration of heteroatom, for example, less than 10 wppm or even having no detectable amount of heteroatom relative to the total weight of material in the heteroatom lean cleavage effluent.

The liquid heteroatom lean cleavage effluent is supplied by line 326 to dehydration reactor 328, where it is contacted with a dehydration catalyst comprising MCM-56 under conditions effective to convert at least a portion of the phenylcyclohexanol to phenylcyclohexene, and create a dehydration effluent. In one embodiment, the dehydration effluent is supplied by line 330 as a second feed to first fractionation column 322 to a tray below that from which the heteroatom lean cleavage effluent in line 326 is withdrawn. By virtue of the relative volatilities of phenylcyclohexene and phenylcyclohexanol, and with proper selection of the second feed location and operation of first fractionation column 322, this allows the phenylcyclohexene so produced to readily exit the column bottoms, while avoiding re-contact with the dehydration catalyst. However, depending on the specific process objectives, the dehydration effluent in line 330 may returned as a second feed to first fractionation column 322, at any location, e.g., feed side section 3B or anti-feed side section 3C, above or below the tray from which the liquid heteroatom lean cleavage effluent in line 326 is withdrawn. Along with phenylcyclohexene, water may also enter first fractionation column 322 with the dehydration effluent in line 330 as a co-product of the dehydration of phenylcyclohexanols in dehydration reactor 328. First fractionation column 322 may be fitted with means (not shown), to properly manage the production of water, e.g., a water boot in a condenser drum on the overhead product circuit with a separate line for withdrawal.

The first bottoms product in line 332, including cyclohexylbenzene, phenylcyclohexenes and heteroatom-containing compounds, e.g., NHPI, the acid-base complexation product or some derivative thereof, is provided to a further separation device, for example, second fractionation column 334. Second fractionation column 334 is operated to separate the first bottoms product into a second overhead product that is removed in line 336 and a second bottoms stream that is removed in line 338. In one embodiment, the second overhead product in line 336 is rich in cyclohexylbenzene and phenylcyclohexene, and has a low concentration of oxygenated hydrocarbons, e.g., no greater than 1000 wppm of oxygenated hydrocarbons, e.g., no greater than 1000 wppm of 1-phenylhexan-1-one. The second overhead product in line 336 is recycled to the oxidation reactor (not shown), optionally after first passing it through a hydrogenation unit to convert phenylcyclohexene to cyclohexylbenzene.

The second bottoms stream in line 338 is rich in heavy oxygenated compounds, e.g., 1-phenylhexan-1-one, phenylcyclohexanones, phenylcyclohexanols, and 6-hydroxyhexaphenone, and contains a low amount of cyclohexylbenzene and phenylcyclohexene, for example, no greater than 5.0 wt %, or no greater than 2.0 wt %, or no greater than 0.1 wt % cyclohexylbenzene and phenylcyclohexene combined. The second bottoms stream further includes the vast majority of the heteroatom-containing compounds that were present in the first bottoms product in line 332, for example, at least 99 wt %, or at least 99.9 wt %, or 100 wt %, relative to the total amount of heteroatom-containing compounds in the first bottoms product. The second bottoms stream will generally be purged from the process.

Figure 4:
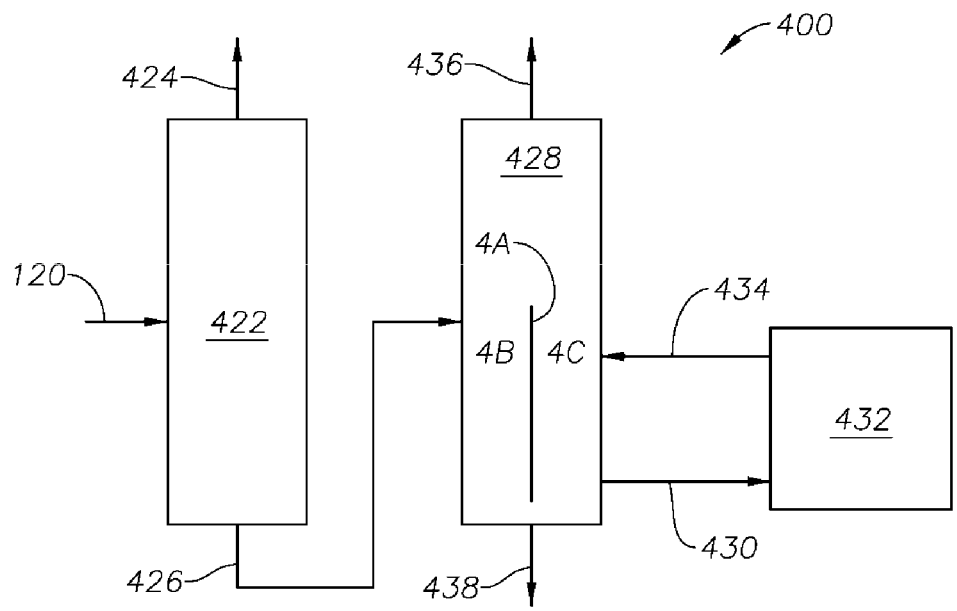
FIG. 4 is a flow diagram of a portion of a process for producing phenol and/or cyclohexanone according to a fourth embodiment of the present application.

A fourth embodiment 400 of the present application is shown in FIG. 4, in which the same oxidation, cleavage and cleavage neutralization steps as the process shown in FIG. 1 are again employed and produce a neutralized cleavage effluent in line 120. The neutralized cleavage effluent is fed by line 120 to a separation device, for example, first fractionation column 422, which is operated to separate the neutralized cleavage effluent into a first overhead product that is removed from column 422 in line 424 and a first bottoms product that is removed in line 426. In one embodiment, the first overhead product in line 424 is rich in phenol, cyclohexanone and components of a lower volatility than phenol, and includes a low amount, for example, no greater than 5.0 wt %, or no greater than 2.0 wt %, or no greater than 0.1 wt %, of cyclohexylbenzene. The first overhead product is fed by line 424 to a product treatment section (not shown) where the phenol and cyclohexanone are recovered and purified.

In the one embodiment, the first bottoms product in line 426 is rich in cyclohexylbenzene, phenylcyclohexanols and components of lower volatility that cyclohexanols. Desirably, the first bottoms product includes a low amount of light components, for example, water, pentanal, hexanal, methylcyclopentanone, cyclohexanone and phenol, comprising no greater than 1.0 wt %, or no greater than 0.1 wt %, or even no greater than 100 wppm of water, pentanal, hexanal, methylcyclopentanone, cyclohexanone and phenol combined. The first bottoms product also contains heteratom compounds derived from one or more of the oxidation catalyst, the cleavage catalyst and the acid-base complexation product resulting from neutralization of the cleavage catalyst.

The first bottoms product is directed by line 426 to a separation device, for example, second fractionation column 428, which comprises a dividing wall 4A running across the entire diameter or fully across a suitable chord of the second fractionation column 428 to form two discrete sections 4B and 4C without vapor or liquid intercommunication. Further, dividing wall 4A runs axially in second fractionation column 428 from a point above the liquid level on the feed tray to which the first bottoms product in line 426 is directed to a point above the reboiler sump liquid level near the bottom of the column 428. Dividing wall 4A ensures that section 4C will not be exposed to the liquid material, and hence the heteroatom-containing compounds, present in the first bottoms product in line 426. Rather, all the liquid in section 4C will come from the reflux generated in the overhead circuit (not shown in FIG. 4) of second fractionation column 428 and flowing down into section 4C. That reflux and hence the liquid in section 4C is derived from a vapor flash of the first bottoms product within second fractionation column 428, i.e., the reboiler vapors from of bottoms circuit (not shown in FIG. 4) flowing up through both sections 4B and 4C. Section 4B is the feed side, while section 4C is the anti-feed side of dividing wall second fractionation column 428.

Second fractionation column 428 is operated to separate from the first bottoms product a second overhead product that is removed in line 436 and is rich in cyclohexylbenzene and phenylcyclohexene, and has a low concentration, e.g., no greater than 1000 wppm, of oxygenated hydrocarbons, an in one embodiment no greater than 1000 wppm of 1-phenylhexan-1-one. The second overhead product in line 436 is recycled to the oxidation reactor (not shown), optionally after first passing it through a hydrogenation unit to convert phenylcyclohexene to cyclohexylbenzene.

Further, second fractionation column 428 is operated to form a second bottoms stream that is removed in line 438 and is rich in heavy oxygenated compounds, e.g., 1-phenylhexan-1-one, phenylcyclohexanones, phenylcyclohexanols, and 6-hydroxyhexaphenone, and contains a low amount of cyclohexylbenzene and phenylcyclohexene, for example, no greater than 5.0 wt %, or no greater than 2.0 wt %, or no greater than 0.1 wt % cyclohexylbenzene and phenylcyclohexene combined. The second bottoms stream in line 438 further includes the vast majority of the heteroatom-containing compounds that were present in the first bottoms product in line 426, for example, at least 99 wt %, or at least 99.9 wt %, or 100 wt %, relative to the total amount of heteroatom-containing compounds in the first bottoms product. The second bottoms stream is generally purged from the process.

Second fractionation column 428 is also operated to withdraw a heteroatom lean cleavage effluent in line 430, as a liquid sidestream from anti-feed side section 4C, conveniently from a tray below the feed tray into which the first bottoms product in line 426 is provided. Conveniently, heteroatom lean cleavage effluent in line 430 is rich in 1-phenylhexan-1-one, phenylcyclohexanols and components of lower volatility than phenylcyclohexanols, and includes a low amount of light components, for example cyclohexylbenzene and phenylcyclohexene, comprising no greater than 50.0 wt %, or no greater than 20 wt %, or even no greater than 5.0 wt % of cyclohexylbenzene and phenylcyclohexene combined. As discussed earlier, the heteroatom lean cleavage effluent in line 430 taken from anti-feed section 4C is derived from a vapor flash of the neutralized cleavage effluent in line 120 of FIG. 4 and will have a very low concentration, for example, less than 10 wppm or even having no detectable amount, of heteroatom-containing compounds relative to the total weight of material in the heteroatom lean cleavage effluent in line 430.

The heteroatom lean cleavage effluent in line 430 is fed to dehydration reactor 432, where it is contacted with a dehydration catalyst comprising MCM-56 under conditions effective to convert at least a portion of the phenylcyclohexanol to phenylcyclohexene, and create a dehydration effluent in line 434. The dehydration effluent is returned as a second feed to second fractionation column 428, conveniently to a tray above that from which the heteroatom lean cleavage effluent in line 430 is withdrawn. By virtue of the relative volatilities of phenylcyclohexene and phenylcyclohexanol, and with proper selection of the second feed location to and operations of second fractionation column 428, this allows the phenylcyclohexene to exit the column overhead, while avoiding re-contact with the dehydration catalyst, and allows unconverted phenylcyclohexanol to readily proceed down the column 428 for withdrawal with the heteroatom lean cleavage effluent in line 130. However, depending on the specific process objectives, the dehydration effluent in line 434 may be returned to second fractionation column 428 at any location, e.g., feed side section 4B or anti-feed side section 4C, above or below the tray from which the liquid heteroatom lean cleavage effluent in line 430 is withdrawn.

Along with phenylcyclohexene, water may also enter second fractionation column 428 as a co-product of the dehydration of phenylcyclohexanols in dehydration reactor 432. Second fractionation column 428 may be fitted with means (not shown), to properly manage the production of water, e.g., a water boot in a condenser drum on the overhead product circuit with a separate line for withdrawal. Additionally, rather than an overhead product, the cyclohexylbenzene and phenylcyclohexene product in line 436 may be taken from second fractionation column 428 as a liquid sidestream at a point near the top of the column, to provide that product with a reduced content of water for subsequent processing and eventual recycle to an oxidation reactor.

It will be appreciated the processes of the above embodiments may also utilize numerous equipment and unit operation elements not shown in the drawings or discussed in their description, including but not limited to heat exchangers through which streams may pass to decrease or increase their temperatures prior to being introduced to another element, and pumps and compressors to provide motive force to the streams, mixers, instrumentation and control valves.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The invention claimed is:

1. A process for producing phenol and/or cyclohexanone, the process comprising:
   (a) contacting cyclohexylbenzene with an oxygen-containing gas to produce an oxidation effluent containing cyclohexylbenzene hydroperoxide;
   (b) contacting at least a portion of the oxidation effluent containing cyclohexylbenzene hydroperoxide with a cleavage catalyst to produce a cleavage effluent containing phenol, cyclohexanone and by-products including phenylcyclohexanol;
   (b1) optionally neutralizing the cleavage effluent to produce a neutralized product thereof;
   wherein the cleavage effluent and/or the neutralized product thereof comprise at least one heteroatom-containing compound;
   (c) separating at least a portion of the at least one heteroatom-containing compound from the cleavage effluent and/or the neutralized product thereof to produce a cleavage fraction containing at least a portion of the phenylcyclohexanol and at least 1.0% less of the at least one heteroatom-containing compound compared to before separating; and
   (d) contacting at least a portion of the cleavage fraction containing phenylcyclohexanol with a dehydration catalyst comprising a molecular sieve of the MCM-22 type to convert at least a portion of the phenylcyclohexanol to phenylcyclohexene.

2. The process of claim 1, wherein the contacting step (a) is conducted in the presence of an oxidation catalyst containing at least one heteroatom and the cleavage effluent produced in step (b) includes at least one heteroatom-containing compound derived from the oxidation catalyst.

3. The process of claim 2, wherein the oxidation catalyst contains nitrogen.

4. The process of claim 2, wherein the oxidation catalyst comprises a cyclic imide.

5. The process of claim 1, wherein the cleavage catalyst contains at least one heteroatom and the cleavage effluent includes at least one heteroatom-containing compound derived from the cleavage catalyst.

6. The process of claim 5, wherein the cleavage catalyst contains sulfur.

7. The process of claim 5, wherein the cleavage catalyst comprises sulfuric acid.

8. The process of claim 1, wherein step (b1) is conducted and comprises contacting the cleavage effluent with a base to form the neutralized product containing an acid-base complexation compound containing at least one heteroatom.

9. The process of claim 8, wherein the base comprises at least one heteroatom.

10. The process of claim 8, wherein the base comprises nitrogen.

11. The process of claim 1, wherein the separating step (c) is conducted in a liquid-vapor flash device.

12. The process of claim 1, wherein the separating step (c) is conducted in a first distillation column.

13. The process of claim 12, wherein the first distillation column comprises a dividing wall distillation column.

14. The process of claim 12, wherein at least a portion of the product produced in the contacting step (d) is fed back to the first distillation column.

15. The process of claim 1, further comprising:
   (f) supplying at least a portion of the phenylcyclohexene produced in the contacting step (d) to the contacting step (a).

16. The process of claim 1, further comprising:
   (g) contacting at least a portion of the phenylcyclohexene produced in the contacting step (d) with hydrogen to convert at least a portion of the phenylcyclohexene to cyclohexylbenzene.

17. The process of claim 16, further comprising:
   (h) supplying at least a portion of the cyclohexylbenzene produced in the contacting step (g) to the contacting step (a).

18. The process of claim 1, wherein at least a portion of the cyclohexylbenzene in the contacting step (a) is produced by alkylation of benzene with cyclohexene.

19. The process of claim 1, wherein at least a portion of the cyclohexylbenzene in step (a) is produced by reaction of benzene with hydrogen in the presence of a hydroalkylation catalyst.

20. The process of claim 19, wherein the hydroalkylation catalyst comprises a solid acid alkylation component and a hydrogenating metal component.

21. The process of claim 20, wherein the solid acid alkylation component comprises a molecular sieve.

22. The process of claim 20, wherein the solid acid alkylation component comprises a molecular sieve of the MCM-22 type.

* * * * *